US010159844B2

(12) United States Patent
Thangaraju et al.

(10) Patent No.: US 10,159,844 B2
(45) Date of Patent: Dec. 25, 2018

(54) IMPLANTABLE MEDICAL DEVICE AND A METHOD FOR OPTIMIZING POWER CONSUMPTION THEREOF

(71) Applicant: HCL Technologies Limited, Noida, Uttar Pradesh (IN)

(72) Inventors: Shyam Thangaraju, Tamil Nadu (IN); Siva Sakthivel Sadasivam, Tamil Nadu (IN)

(73) Assignee: HCL Technologies Limited, Noida (IN)

( * ) Notice: Subject to any disclaimer, the term of this patent is extended or adjusted under 35 U.S.C. 154(b) by 0 days.

(21) Appl. No.: 14/975,418

(22) Filed: Dec. 18, 2015

(65) Prior Publication Data

US 2016/0220831 A1    Aug. 4, 2016

(30) Foreign Application Priority Data

Jan. 29, 2015 (IN) .............................. 266/DEL/2015

(51) Int. Cl.
*A61N 1/00* (2006.01)
*A61N 1/372* (2006.01)
*A61N 1/39* (2006.01)

(52) U.S. Cl.
CPC ..... *A61N 1/37276* (2013.01); *A61N 1/37217* (2013.01); *A61N 1/3956* (2013.01)

(58) Field of Classification Search
USPC ......................................................... 607/60
See application file for complete search history.

(56) References Cited

U.S. PATENT DOCUMENTS

| 6,083,248 | A | * | 7/2000 | Thompson | ........... A61B 5/0031 |
| | | | | | 607/30 |
| 7,079,977 | B2 | | 7/2006 | Osorio et al. | |
| 8,641,646 | B2 | | 2/2014 | Colborn | |
| 2002/0016568 | A1 | * | 2/2002 | Lebel | ................ A61M 5/14276 |
| | | | | | 604/131 |
| 2008/0217400 | A1 | * | 9/2008 | Portano | .................. G06Q 20/04 |
| | | | | | 235/380 |
| 2009/0088821 | A1 | * | 4/2009 | Abrahamson | ......... H04J 3/0667 |
| | | | | | 607/60 |

OTHER PUBLICATIONS

HervéAubert, RFID Technology for Human Implant Devices, Special issue on nanosciences /nanotechnologies, Mar. 1, 2011, Number of pp. 18, France.

* cited by examiner

*Primary Examiner* — Nicole F Johnson
(74) *Attorney, Agent, or Firm* — Knobbe Martens Olson & Bear LLP

(57) ABSTRACT

The present disclosure discloses an implantable medical device and a method for optimizing power consumption of the implantable medical device. The implantable medical device comprises a time synchronization unit, a decoder, and a processor. The time synchronization unit may receive a time signal transmitted by an atomic clock of a satellite using radio waves upon occurrence of an event. The event may be an internal command or an external command to activate the time synchronization unit. Further, the decoder may decode the time signal in order to obtain a time data. Further, the processor may generate a log of the time data and metadata. The metadata indicates physiological parameters of a patient. The implantable medical device further comprises an amplifier to amplify the time signal carrying the time data when strength of the time signal is in a predefined range.

8 Claims, 2 Drawing Sheets

IMPLANTABLE MEDICAL DEVICE AND A METHOD FOR OPTIMIZING POWER CONSUMPTION THEREOF

CROSS-REFERENCE TO RELATED APPLICATIONS AND PRIORITY

The present application claims benefit from Indian Complete Patent Application No. 266/DEL/2015, filed on Jan. 29, 2015, the entirety of which is hereby incorporated by reference.

TECHNICAL FIELD

The present subject matter described herein, in general, relates to an implantable medical device and a method for optimizing power consumption of the implantable medical device.

BACKGROUND

Implantable medical devices are generally used for delivering minute quantities of drug to a patient suffering from neurological disorders or endocrine disorders. The implantable medical devices, for example cardiac rhythm management (CRM) devices, are surgically or medically introduced into the patient's body and intended to remain after the procedure. Functionalities performed by the implantable medical devices are, for example, providing electrical stimulation, providing magnetic stimulation, drug infusion, controlling brain temperature and the like. For performing these functionalities, a power is required for the implantable medical devices. The power is provided by using a battery in the implantable medical devices. Since the battery's life is limited, it restricts the usage of the implantable medical devices.

Specially, when the batteries are used for powering up a real-time clock (RTC) present in the integrated circuit (IC) of the implantable medical devices. The job of the RTC is to maintain a log of time and physiological details in the implantable device. Further, these log details are transmitted to a wirelessly connected an external monitoring terminal used for monitoring the activities of the implantable device. For maintaining the log details, the RTC is required to be always ON which consumes a significant amount of the battery's power. This consistent consumption of the battery's power leads the battery into dead state. Thus, optimizing the power consumption of the batteries of the implantable medical devices is a major concern.

SUMMARY

This summary is provided to introduce aspects related to an implantable medical device and methods for optimizing power consumption of the medical device are further described below in the detailed description. This summary is not intended to identify essential features of subject matter nor is it intended for use in determining or limiting the scope of the subject matter.

In one implementation, an implantable medical device is disclosed. The implantable medical device comprises a time synchronization unit, a decoder, a processor, a memory, and an input/output interface. The time synchronization unit may receive a time signal transmitted by an atomic clock of a satellite using radio waves upon occurrence of an event. The event may be an internal command or an external command to activate the time synchronization unit. The internal command may be executed at predefined time intervals. The external command may be executed on a need only basis when the implantable medical device needs to be activated. Further, the decoder may decode the time signal in order to obtain a time data. Further, the processor may generate a log of the time data and metadata. The metadata indicates physiological parameters of a patient. The implantable medical device further comprises an amplifier to amplify the time signal carrying the time data based on strength of the time signal.

In another implementation, a method for optimizing a power consumption of an implantable medical device is disclosed. The method may comprise receiving, by a time synchronization unit, time signal transmitted by an atomic clock of a satellite using radio waves upon occurrence of an event. The event may be an internal command or an external command to activate the time synchronization unit. The internal command may be executed at predefined time intervals. The external command may be executed on a need only basis when the implantable medical device needs to be activated. The method may further comprise decoding, by a decoder, the time signal in order to obtain a time data. Further, the method may comprise generating, by a processor, a log of the time data and metadata. Further, the metadata indicates physiological parameters of a patient. The method may further comprise amplifying, by using an amplifier, the time signal carrying the time data based on strength of the time signal.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Figure 1:
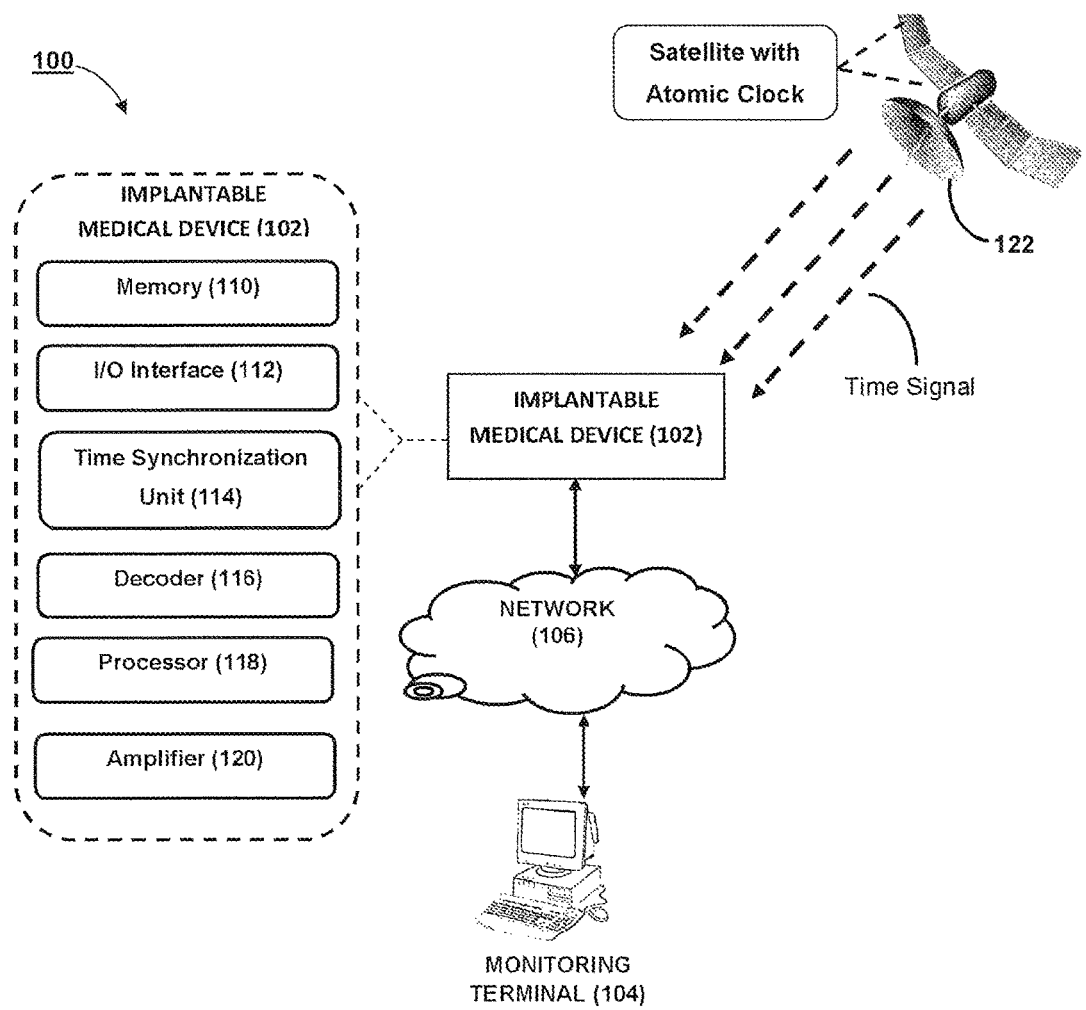
FIG. 1 illustrates a network implementation illustrating communication between an implementable medical device, a monitoring terminal, and a satellite for optimizing power consumption of the implantable medical device, in accordance with an embodiment of the present disclosure.

Referring to FIG. 1, a network implementation 100 of an implantable medical device 102, a monitoring terminal, and a satellite 122, for optimizing power consumption of the implantable medical device 102 is illustrated, in accordance with an embodiment of the present subject matter. Although the present subject matter is explained considering that the monitoring terminal 104 is implemented on a server, it may be understood that the monitoring terminal 104 may also be implemented in a variety of computing systems, such as a laptop computer, a desktop computer, a notebook, a workstation, a mainframe computer, a server, a network server, a tablet, a mobile phone, and the like. According to embodiment of present disclosure, the implantable medical device 102 may be implanted into a patient's body. Further, the implantable medical device 102 may communicate with the satellite 122 using radio frequency (RF) waves. According to embodiments of present disclosure, the implantable medical device 102 may be communicatively coupled to the monitoring terminal 104 through a network 106.

In one implementation, the network 106 may be a wireless network, a wired network or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

The implantable medical device 102 illustrated in the FIG. 1 may further comprises a memory 110, an input/output (I/O) interface 112, a time synchronization unit 114, a decoder 116, a processor 118, and an amplifier 120. The processor 118 may be implemented as one or more microprocessors, microcomputers, microcontrollers, digital signal processors, central processing units, state machines, logic circuitries, and/or any devices that manipulate signals based on operational instructions.

The I/O interface 112 may include a variety of software and hardware interfaces, for example, a web interface, a graphical user interface, and the like. The I/O interface 112 may allow the implantable medical device 102 to interact with the monitoring terminal 104. Further, the I/O interface 112 may enable the implantable medical device 102 to communicate with other computing devices, such as web servers and external data servers (not shown). The I/O interface 112 can facilitate multiple communications within a wide variety of networks and protocol types, including wireless networks, such as WLAN, cellular, or satellite.

The memory 110 may include any computer-readable medium and computer program product known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

According to embodiments of present disclosure, the implantable medical device 102 and method for optimizing power consumption of the implantable medical device 102 are described in detail. Battery is required for providing power to the implantable medical device 102. Since the battery's life is limited, it becomes a major pain point for the implantable medical device 102. One of the noncore functions of the battery is to power a real-time clock (RTC) present in an integrated circuit (IC) of the implantable medical device 102. Sometimes, a separate battery may be required for powering standalone RTC in the implantable medical devices. Since the function of the RTC is to maintain a time log, it consistently remains ON which results in higher consumption of the battery.

But, most of implantable medical devices require time data only on a need basis and don't require a permanent clock such as RTC. For example, the implantable medical device 102 (such as a defibrillator) will need to monitor the electrocardiogram (ECG) of a patient and if it detects a fibrillation, it sends a direct current (DC) shock to correct the irregularity in cardiac rhythm Thus, the implantable medical device (defibrillator) will be required to maintain a log of time and dosage of the shock delivered only when it realizes that the DC shock has to be delivered into the patient's body.

In another example, the implantable medical device 102 (such as a drug delivery system) which delivers a pain killer to the spinal cord will be required to maintain a log of time and dosage of the pain killer drug delivered when it is asked to do by an external user controlled device/monitoring terminal 104. Yet in another example, the implantable medical device 102 (such as a closed loop diabetes management device) will have an insulin pump that gets the blood glucose data from a Continuous glucose monitoring (CGMS) and decides to administer insulin when the glucose value is high. The insulin pump will be required to maintain a log of time and dosage of the insulin delivered. Thus, it may be observed from the above examples that the implantable medical devices may require to maintain the log of the time data only when the need arises and therefore, the permanent RTC is not required. In other words, the implantable medical device 102 may only require a timer, instead of the RTC, for maintaining the log of the time.

Thus, to avoid such unnecessary use of the battery for powering the RTC, the present disclosure may utilize different satellites 122 which transmits time signal through radio frequency (RF) waves which are freely available throughout the world. These satellites 122 relay the time signal from atomic clocks they have on board using the radio frequency waves. According to embodiments of present disclosure, the time synchronization unit 114, of the implantable medical device 102, may receive the time signal transmitted by the atomic clock of the satellite 122 using radio waves upon occurrence of an event. According to embodiments, the time synchronization unit 114 may further comprises a radio frequency (RF) antenna for receiving the time signal.

Further, the event may be an internal command or an external command which may be required for activating the time synchronization unit 114. The internal command may be executed at a predefined interval which may be set by a user, for example 1 hour, to wake up the time synchronization unit 114. Further, the external command may be executed on a need only basis when the implantable medical device 102 needs to be activated. For example, as soon as the implantable medical device 102 (defibrillator) realizes that it is about to perform a function of delivering the DC shock, it will wake up the time synchronization unit 114 for obtaining the time signal from any available overhead satellite 122 with open sharing of the time. This way, the external command may be provided only of the need basis when the implantable medical device 102 needs to be activated. According to some embodiments of present disclosure, the external command may also be provided by the monitoring terminal 104 for activating the time synchronization unit 114.

Further, the time signal received may be weak or of low strength in some areas. In such cases, the amplifier 120, of the implantable medical device 102, may amplify the time signal. The amplifier 120 may be in the minimum amplification mode to conserve the battery. As the time signal becomes undetectable, the amplifier 120 may increase the amplification factor till it can acquire the time signal. Once the time signal is not obtainable even at the highest amplification factor, the amplifier 120 may send a warning and takes a log of that. Further, the decoder 116, of the implantable medical device 102, may decode the time signal in order to obtain a time data. Further, the processor 118, of the implantable medical device 102, may generate a log of the time data and metadata. The metadata may indicate physiological parameters, of the patient, which may be obtained after the activation of the implantable medical device 102.

Thus, by activating the time synchronization unit 114 on need only basis the usage of the battery may be minimized, thereby optimizing the power consumption of the implantable medical device 102. Also, the radio frequency (RF) antenna of the time synchronization unit 114 is substantially cheaper than a dedicated RTC. Further, it may be noted to a person skilled in art that the optimization technique disclosed in the present disclosure may be implemented in any implantable devices other than the implantable medical device 102.

Figure 2:
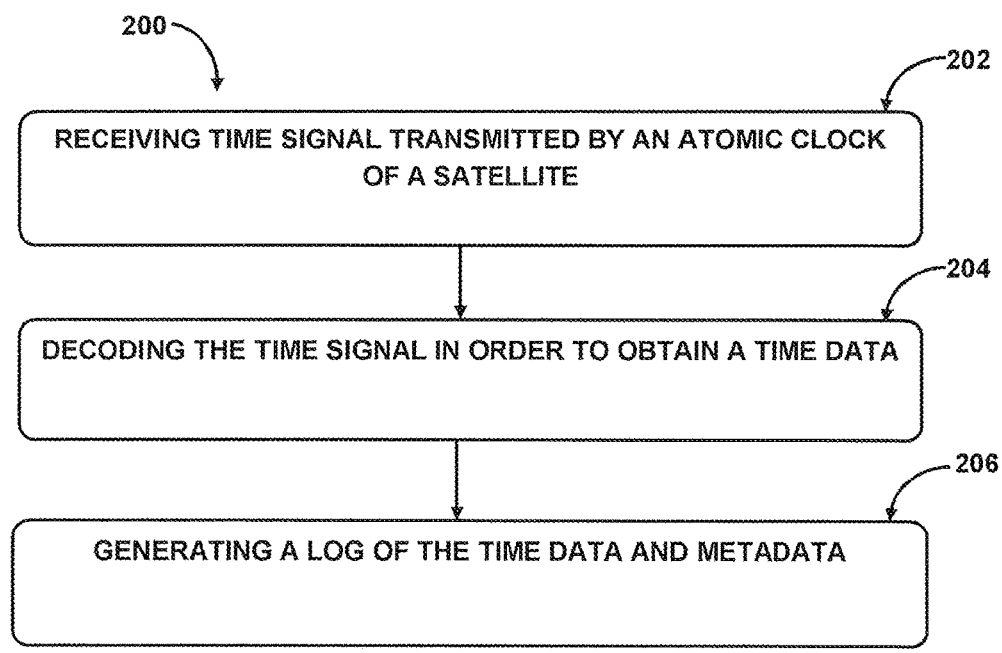
FIG. 2 illustrates a method for optimizing power consumption of the implantable medical device, in accordance with an embodiment of the present disclosure.

Referring now to FIG. 2, the method of optimizing power consumption of the implantable medical device is shown, in accordance with an embodiment of the present subject matter. The order in which the method 200 is described is not intended to be construed as a limitation, and any number of the described method blocks can be combined in any order to implement the method 200 or alternate methods. Additionally, individual blocks may be deleted from the method 200 without departing from the spirit and scope of the subject matter described herein. Furthermore, the method can be implemented in any suitable hardware, software, firmware, or combination thereof. However, for ease of explanation, in the embodiments described below, the method 200 may be considered to be implemented in the above described implantable medical device 102.

At block 202, time signal transmitted by an atomic clock of a satellite using radio waves may be received, upon occurrence of an event. Further, the event may be an internal command or an external command to activate the time synchronization unit.

At block 204, the time signal is decoded by a decoder in order to obtain a time data.

At block 206, a log of the time data and metadata may be generated. The metadata indicates physiological parameters of a patient.

Although implementations for implantable medical device and method for optimizing power consumption of the implantable medical device have been described in language specific to structural features and/or methods, it is to be understood that the appended claims are not necessarily limited to the specific features or methods described. Rather, the specific features and methods are disclosed as examples of implementations for optimizing power consumption of the implantable medical device.

What is claimed is:

1. An implantable medical device comprising:
   a time synchronization unit receives a time signal from a satellite having onboard atomic clocks by using radio waves, wherein the time signal is received upon occurrence of an event, and wherein the event is occurred on activation of an internal command or an external command;
   a decoder to decode the time signal in order to obtain a time data; and
   a processor configured to trigger a timer for maintaining a time log, indicating the time data along with metadata, without maintaining a Real-Time Clock (RTC), wherein the metadata indicates physiological parameters of a patient.

2. The implantable medical device of claim 1, further comprise an amplifier to amplifying the time signal carrying the time data based on strength of the time signal, wherein the amplifier generates a warning signal when the time signal is obtainable at a highest amplification factor.

3. The implantable medical device of claim 1, wherein the internal command is executed at predefined time intervals.

4. The implantable medical device of claim 1, wherein the external command is executed on a need only basis when the implantable medical device needs to be activated.

5. A method for optimizing a power consumption of an implantable medical device, wherein the method comprising:
   receiving, by a time synchronization unit, a time signal from a satellite having onboard atomic clocks by using radio waves, wherein the time signal is received upon occurrence of an event, and wherein the event is occurred on activation of an internal command or an external command;
   decoding, by a decoder, the time signal in order to obtain a time data; and
   triggering, by a processor, a timer for maintaining time log, indicating the time data along with metadata, without maintaining a Real-Time Clock (RTC), wherein the metadata indicates physiological parameters of a patient.

6. The method of claim 5, further comprising
   amplifying, by using an amplifier, the time signal carrying the time data based on strength of the time signal, and
   generating, by the amplifier, a warning signal when the time signal is obtainable at a highest amplification factor.

7. The method of claim 5, wherein the internal command is executed at predefined time intervals.

8. The method of claim 5, wherein the external command is executed on a need only basis when the implantable medical device needs to be activated.

* * * * *